United States Patent
Brazdil, Jr. et al.

(10) Patent No.: US 6,262,290 B1
(45) Date of Patent: Jul. 17, 2001

(54) AMELIORATION OF AMMONIA BREAKTHROUGH IN AN ALKANE AMMOXIDATION PROCESS

(75) Inventors: James F. Brazdil, Jr., Glen Ellyn, IL (US); Joseph P. Padolewski, Akron, OH (US)

(73) Assignee: The Standard Oil Company, Chicago, IL (US)

( * ) Notice: Subject to any disclaimer, the term of this patent is extended or adjusted under 35 U.S.C. 154(b) by 0 days.

(21) Appl. No.: 09/633,243

(22) Filed: Aug. 7, 2000

(51) Int. Cl.[7] .................................................. C07C 253/00

(52) U.S. Cl. .............................................................. 558/319

(58) Field of Search ............................................... 558/319

(56) References Cited

U.S. PATENT DOCUMENTS 5,973,186 * 10/1999 Midorikawa et al. ............... 558/319

* cited by examiner

*Primary Examiner*—Cecilia Tsang
*Assistant Examiner*—Joseph Murray
(74) *Attorney, Agent, or Firm*—David P. Yusko

(57) ABSTRACT

The invention is a method for the reduction of ammonia breakthrough during the manufacture of acrylonitrile comprising introducing a hydrocarbon selected from the group consisting of propane and isobutane; ammonia and an oxygen-containing gas into a lower portion of a fluid-bed reactor containing an ammoxidation catalyst to react in the presence of said catalyst to produce acrylonitrile. The method comprises introducing into the reactor at least one $C_2$ to $C_5$ olefin which will react with at least a portion of the unreacted ammonia and oxygen present in the reactor to substantially reduce the amount of ammonia present in the reactor effluent exiting the reactor.

15 Claims, No Drawings

AMELIORATION OF AMMONIA BREAKTHROUGH IN AN ALKANE AMMOXIDATION PROCESS

BACKGROUND OF THE INVENTION

1. Field of the Invention

The present invention is related to the manufacture of acrylonitrile by the direct ammoxidation of a saturated hydrocarbon (e.g., propane), ammonia and oxygen in a reactor containing an ammoxidation catalyst. More specifically, the invention is related to the substantial reduction of unreacted ammonia, ammonium salts and resulting waste products produced from the unreacted ammonia. In particular, the invention relates to the addition of $C_2$–$C_5$ olefin to the reactor to react with the unreacted ammonia thereby reducing and/or eliminating unreacted ammonia from the reactor effluent. This substantial reduction of ammonia in the reactor effluent provides significant environmental and economic advantages.

This invention has particular utility in the conversion of existing propylene based feed acrylonitrile plants to propane based feed acrylonitrile plants.

2. Description of the Prior Art

The production of acrylonitrile from propane is an emerging technology. While there are numerous patents related to catalysts and processing schemes for such technology. Commercialization of this technology has not yet occurred and acrylonitrile continues to be produced throughout the world via the ammoxidation of propylene (a more expensive feedstock than propane).

For both the ammoxidation of propylene and propane to acrylonitrile, ammonia is a required feedstock. Typically, unreacted ammonia remains in the reactor effluent, a condition known as "ammonia breakthrough". In order to remove unreacted ammonia in commercial propylene based processes, the reactor effluent is contacted with a sulfuric acid quench to form ammonium sulfate which is then removed from the process as an aqueous waste stream which is then deep-welled or subjected to biological treatment.

In processes for the fluid-bed ammoxidation of propylene to acrylonitrile, U.S. Pat. Nos. 5,288,473 and 5,457,223 teach the substantial reduction of ammonia in the reactor effluent by the strategic addition of an oxygenate compound, preferably methanol, to the reactor.

An object of the present invention is a solution to ammonia breakthrough in processes for the ammoxidation of propane or isobutane to acrylonitrile.

A further object of the instant invention is an economical process scheme for the conversion of a propylene feed acrylonitrile plant to a propane or isobutane feed plant.

SUMMARY OF THE INVENTION

The invention is a method for the reduction of ammonia breakthrough in processes for the manufacture of acrylonitrile from propane and/or isobutane. More specifically, the invention is a process for the manufacture of acrylonitrile comprising introducing a hydrocarbon selected from the group consisting of propane and isobutane; ammonia and an oxygen-containing gas into a lower portion of a fluid-bed reactor containing an ammoxidation catalyst, and then reacting the hydrocarbon, ammonia and oxygen in the presence of said catalyst to produce acrylonitrile, wherein the improvement comprising introducing into the reactor at least one $C_2$ to $C_5$ olefin which will react with at least a portion of the unreacted ammonia and oxygen present in the reactor to substantially reduce the amount of ammonia present in the reactor effluent exiting the reactor.

The significance of the process in the present invention is that it provides a simple and economic procedure for the substantial elimination of ammonia breakthrough (i.e., unreacted $NH_3$) in a fluid-bed reactor along with the additional advantage of eliminating ammonium sulfate as a by-product during the manufacture of acrylonitrile. The elimination of ammonium sulfate from the waste stream during acrylonitrile manufacture means that the waste stream does not contain any or only a minimal amount of ammonium salts. This leads to a significant economic advantage in the production of acrylonitrile, especially if one cannot practice deep-well injection. Without a substantial reduction in ammonia in the reactor effluent, the waste stream emanating from the quench column would contain ammonium sulfate $(NH_4)_2SO_4$ in a fairly high concentration making disposal of this stream in an economic and environmentally acceptable manner more difficult. The minimization or the elimination of the ammonium sulfate from this stream can make these streams acceptable to waste treatment procedures which do not require severe conditions or expensive materials of construction leading to significant economic and environmental advantages.

The present invention thus reduces or eliminates the amount of ammonia that escapes from the reactor and therefore minimizes or eliminates the cost required to quench, recover, dispose of, or recycle the unreacted ammonia. Furthermore, the invention provides an added benefit of producing additional useful products from the olefin.

Another embodiment of the instant invention is a method for the conversion of a propylene based feedstock acrylonitrile manufacturing process, wherein propylene, ammonia and oxygen are reacted in a reactor in the presence of a catalyst to produce acrylonitrile, to a propane based feedstock acrylonitrile manufacturing process, wherein propane, ammonia and oxygen are reacted in the presence of a catalyst to produce acrylonitrile. This method comprises:

(a) substituting a propane based feedstock for the propylene based feedstock, (b) introducing into the reactor at least one $C_2$ to $C_5$ olefin which will react with at least a portion of unreacted ammonia and oxygen present in the reactor to substantially reduce the amount of ammonia present in the reactor effluent exiting the reactor, and (c) adding to the process a means for the separation, recovery and recycle of unreacted propane.

An advantage of this embodiment is the ability to convert the plant from propylene based feedstocks to lower cost propane based feedstocks at a lower overall capital cost than needed to build a new propane based feedstock plant through the maximum use of existing equipment.

DETAILED DESCRIPTION OF THE INVENTION

The present invention reduces the production of ammonium sulfate generated during the manufacture of acrylonitrile from the reaction of propane and/or isobutane, ammonia and oxygen by adding at least one $C_2$–$C_5$ olefin to the reactor. The addition of the $C_2$–$C_5$, olefin allows for the substantial or complete reaction of excess ammonia in the reactor with the olefin which in turn leads to substantial or complete elimination of ammonium sulfate from the waste stream emanating from the quench column of an acrylonitrile plant. Moreover, the reaction of the $C_2$–$C_5$ olefin with excess ammonia provides for the additional production of useful products (e.g. the reaction of propylene to acrylonitrile).

In the preferred practice of the present invention, propane, ammonia and air react in the presence of a catalyst in a fluid-bed catalytic reactor to produce acrylonitrile. In such reactors, the propane, ammonia and air are introduced at or near the base of the reactor, the gaseous reactants rise through the catalyst bed while reacting to produce acrylonitrile. The reaction products, by-products and unreacted feeds exit at or near the top of the reactor.

Any catalyst capable of catalyzing the reaction of propane and/or isobutane in contact with ammonia and oxygen to yield acrylonitrile and/or methacrylonitrile is suitable for the instant invention. One such catalyst is described by the following general formula:

$$V_vSb_mA_aD_dO_x$$

wherein A, when present, is at least one of Sn, Ti, and Fe,

D, when present, is at least one of Li, Mg, Na, Ca, Sr, Ba, Co, Cr, Ga, Ni, Zn, Ge, Nb, Zr, Mo, W, Cu, Te, Ta, Se, Bi, Ce, In, As, B, Al, and Mn.

V is 1 m is 0.5 to 10 a is 0 to 10 d is 0 to 10 x is a value sufficient to satisfy the valence requirements of the other elements present.

These catalysts may be either unsupported or supported on a suitable carrier. Typical suitable carriers, also known as "supports", include silica, alumina, zirconia, titanium and their combinations. Silica is the preferred support.

In the practice of the instant invention, the $C_2$–$C_5$ olefin may be introduced into the reactor at any suitable point downstream from the point where propane and/or isobutane are fed to the reactor. Preferably, the olefin is introduced as a point ownstream from the alkane feed where the olefin will have an opportunity to react ith substantially all or all of the excess ammonia but not be competitive with the main alkane ammoxidation reaction occurring in the lower portion of the catalyst bed. In one embodiment relating to fluid-bed reactors, the location of the olefin feed should be above 20% of the level of the expanded catalyst bed height, preferably at a location above 50% of the level of the expanded catalyst bed height, more preferably at a location above 80% of the level of the expanded catalyst bed height.

Any $C_2$ to $C_5$ olefin will provide the benefits of the instant invention. Propylene is preferred because of its availability and because it will react with oxygen and ammonia to produce acrylonitrile.

The amount of olefin can vary but should be enough to react with any excess ammonia breaking through into the reactor effluent. Any unreacted olefin, as well as any unreacted alkane, making its way into the reactor effluent can be recovered and recycled into the reactor. The hydrocarbon and recycle system may consist of any method known in the art for separating gaseous hydrocarbons from other gaseous components. Suitable methods include, but are not limited to, refrigeration and compression (i.e. fractionation), or pressure swing adsorption and desorption as disclosed in U.S. Pat. No. 5,532,384, or temperature swing adsorption and desorption among others.

The olefin can be injected next, or in the presence of a suitable diluent gas such as nitrogen, steam, air, CO, $CO_2$, recycled off gas or combinations thereof.

Most acrylonitrile produced in the world today is produced using fluid-bed reactors. However, the instant invention has utility not only with conventional fluid-bed reactors but also with any reactor capable of maintaining the catalyst in a fluid state such as transport line reactors, riser reactors or recycle rectors. The instant invention may also be utilized with fixed bed reactors.

Each propane ammoxidation catalyst operates at somewhat different feed ratios and operating conditions for maximum acrylonitrile yield and/or economic considerations. The amount of excess ammonia exiting the reactor from a propane ammoxidation reactor will vary somewhat depending on the catalyst used. The level of olefin to be added will vary according to the catalyst types and the nature of the reactor. Accordingly, in the practice of the present invention, the amount of olefin fed into the reactor will be dictated by the conditions and the catalyst used. In terms of a catalyst which operates in a lean oxygen phase, it may be necessary to add additional oxygen to the reactor. However, catalyst which would operate in an excess of oxygen would not have the necessity for the addition of any oxygen to the reactor. Typically, any ammoxidation catalyst may be utilized in the practice of the present invention.

As stated previously, each propylene/propane ammoxidation catalyst will operate at somewhat different feed ratios and operating conditions. Conventional operating condition and feed ratio for the manufacture of acrylonitrile as set forth in U.S. Pat. Nos. 3,911,089 and 4,873,215 are suitable and herein incorporated by reference. Typical reaction parameters are as follows. Reactor temperatures are between 300° C. and 600° C. The pressure inside the reactor is between about 1 and about 10 atmospheres. Ammonia is fed to the reactor in a molar ratio of 0.01 to 5 ammonia to 1 propane, preferably of 0.01 to 1 ammonia to 1 propane, more preferably of 0.06 to 0.4 ammonia to 1 propane. Oxygen is fed to the reactor in a molar ratio of 0.1 to 5 oxygen to 1 propane, preferably of 0.1 to 2 oxygen to 1 propane, more preferably of 0.1 to 1 oxygen to 1 propane. The diluent gas may be fed to the reactor in a molar ratio of 0 to 100 diluent to 1 propane, preferably of 0 to 10 diluent to 1 propane. The $C_2$ to $C_5$ olefin is fed to the reactor in a molar ratio of 0.001 to 100 olefin to 1 propane, preferably of 0.01 to 1 olefin to 1 propane, more preferably of 0.01 to 0.1 olefin to 1 propane.

During the practice of the process of the present invention the standard operating condition at which the existing propylene/propane catalyst has been operated should not have to be changed but can be changed depending upon feed and catalyst conditions. For example, if the catalyst utilized operates under a low or minimal oxygen environment there may be a necessity to increase the amount of oxygen into the reactor to insure that the process of the present invention operates most efficiently. This may be accomplished by increasing the oxygen ratio in the feed or actually supplying oxygen to the reactor by a separate means.

The present invention is particularly suitable for the conversion of acrylonitrile plants from propylene based feedstocks to propane based feedstocks. The substitution for propylene based feedstocks with lower cost propane based feedstocks significantly reduces the commercial manufacturing cost of acrylonitrile in an existing commercial plant. Further, a key advantage of the process described herein is the ability to convert the plant from propylene to propane based feedstocks at a lower capital cost than needed to build a new propane based feedstock plant through the maximum use of existing equipment.

Since, with current catalysts and technology, the single pass conversion of propane to acrylonitrile is less than the single pass conversion of propylene to acrylonitrile, unreacted propane is typically separated and recovered from the reactor effluent and then recycled to the reactor. As such, a key component for the conversion of a propylene based plant to an propane based plant is the additional plumbing and hardware associated with the separation, recovery and recycle of the propane. Typically, the catalyst employed in the reactor would also be replaced with a catalyst more suitable to the ammoxidation of propane to acrylonitrile. An advantage of the process described herein for such plant conversions is that the use of small quantities of propylene to reduce or eliminate the amount of unreacted ammonia from the reactor precludes the need to make other modifications in the quench, recovery, and purification components of the existing propylene based acrylonitrile plant. Therefore, an existing single pass propylene feedstock acrylonitrile plant may economically be converted to a recycle alkane feedstock process with only the minimal addition of capital equipment. Moreover, such a conversion may be accomplished without adversely affecting the quality and commercial specifications of the products of the plant.

Lastly, the process and the method of operation described herein is particularly suitable for propylene based acrylonitrile plants which have been converted to a propane feedstock in that such plants are likely to have propylene storage on site or propylene otherwise available to the plant.

SPECIFIC EMBODIMENTS

For purposes of illustration only, the following examples are set forth to describe the process of the present invention.
Comparative Example A Using a 0.5 inch diameter titanium U-tube reactor positioned in a temperature controlled sand bath at 480° C., a gas feed consisting of 3 propane/0.78 ammonia/2.2 oxygen/2.2 nitrogen/1 water was introduced into the bottom of the reactor containing a promoted vanadium, antimony oxide propane ammoxidation catalyst diluted 50 wt % with quartz chips. The reactor was operated at atmospheric pressure and the weight hourly space velocity of the propane feed was 0.42 $hr^{-1}$. Propane conversion was 18.2%. Selectivity to acrylonitrile was 58.1%. Total useful product selectivity (i.e. acrylonitrile, acrolein, and acrylic acid) was about 58.1%. The amount of ammonia breakthrough was 22.3% of the ammonia fed.

EXAMPLE 1

Using a 0.5 inch diameter titanium U-tube reactor positioned in a temperature controlled sand bath at 480° C., a gas feed consisting of 3 propane/0.72 ammonia/2.2 oxygen/2.2 nitrogen/1 water was introduced into the bottom of the reactor containing a promoted vanadium, antimony oxide propane ammoxidation catalyst diluted 50 wt % with quartz chips. The reactor was operated at atmospheric pressure and the weight hourly space velocity of the propane feed was 0.45 $hr^{-1}$. Propylene was introduced into the reactor at 81.4% of the level of the catalyst bed height. The overall ratio of propylene to propane fed to the reactor was 0.037/1. Conversion of propane plus propylene was 18.4%. Selectivities to useful products from propane and propylene were: 57.6% to acrylonitrile, 0.1% to acrolein, and 0.3% to acrylic acid (total useful product selectivity of 58.1%). The amount of ammonia breakthrough was reduced to 14.7% of the ammonia fed.

EXAMPLE 2

Using a 0.5 inch diameter titanium U-tube reactor positioned in a temperature controlled sand bath at 480° C., a gas feed consisting of 3 propane/0.74 ammonia/2.2 oxygen/2.2 nitrogen/1 water was introduced into the bottom of the reactor containing a promoted vanadium, antimony oxide propane ammoxidation catalyst diluted 50 wt % with quartz chips. The reactor was operated at atmospheric pressure and the weight hourly space velocity of the propane feed was 0.44 $hr^{-1}$. Propylene was introduced into the reactor at 81.4% of the level of the catalyst bed height. The overall ratio of propylene to propane fed to the reactor was 0.053/1. Conversion of propane plus propylene was 19.1%. Selectivities to useful products from propane and propylene were: 57.6% to acrylonitrile, 0.3% to acrolein, and 1.2% to acrylic acid (total useful product selectivity of 59.0%). The amount of ammonia breakthrough was reduced to 14.0% of the ammonia fed.

EXAMPLE 3

Using a 0.5 inch diameter titanium U-tube reactor positioned in a temperature controlled sand bath at 480° C., a gas feed consisting of 3 propane/0.74 ammonia/2.2 oxygen/2.2 nitrogen/1 water was introduced into the bottom of the reactor containing a promoted vanadium, antimony oxide propane ammoxidation catalyst diluted 50 wt % with quartz chips. The reactor was operated at atmospheric pressure and the weight hourly space velocity of the propane feed was 0.46 $hr^{-1}$. Propylene was introduced into the reactor at 81.4% of the level of the catalyst bed height. The overall ratio of propylene to propane fed to the reactor was 0.097/1. Conversion of propane plus propylene was 18.6%. Selectivities to useful products from propane and propylene were: 58.6% to acrylonitrile, 1.1% to acrolein, and 2.9% to acrylic acid (total useful product selectivity of 62.6%). The amount of ammonia breakthrough was reduced to 13.9% of the ammonia fed.

EXAMPLE 4

Using a 0.5 inch diameter titanium U-tube reactor positioned in a temperature controlled sand bath at 480° C., a gas feed consisting of 3 propane/0.71 ammonia/2.2 oxygen/2.2 nitrogen/1 water was introduced into the bottom of the reactor containing a promoted vanadium, antimony oxide propane ammoxidation catalyst diluted 50 wt % with quartz chips. The reactor was operated at atmospheric pressure and the weight hourly space velocity of the propane feed was 0.45 $hr^{-1}$. Propylene was introduced into the reactor at 49.1% of the level of the catalyst bed height. The overall ratio of propylene to propane fed to the reactor was 0.073/1. Conversion of propane plus propylene was 20.4%. Selectivities to useful products from propane and propylene were: 55.3% to acrylonitrile, 0.2% to acrolein, and 4.0% to acrylic acid (total useful product selectivity of 59.5%). The amount of ammonia breakthrough was reduced to 11.1% of the ammonia fed.

EXAMPLE 5

Using a 0.5 inch diameter titanium U-tube reactor positioned in a temperature controlled sand bath at 480° C., a gas feed consisting of 3 propane/0.69 ammonia/2.2 oxygen/2.2 nitrogen/1 water was introduced into the bottom of the reactor containing a promoted vanadium, antimony oxide propane ammoxidation catalyst diluted 50 wt % with quartz chips. The reactor was operated at atmospheric pressure and the weight hourly space velocity of the propane feed was 0.47 $hr^{-1}$. Propylene was introduced into the reactor at 49.1% of the level of the catalyst bed height. The overall ratio of propylene to propane fed to the reactor was 0.103/1. Conversion of propane plus propylene was 21.2%. Selectivities to useful products from propane and propylene were: 50.8% to acrylonitrile, 3.9% to acrolein, and 6.5% to acrylic acid (total useful product selectivity of 61.3%). The amount of ammonia breakthrough was reduced to 8.1% of the ammonia fed.

EXAMPLE 6

Using a 0.5 inch diameter titanium U-tube reactor positioned in a temperature controlled sand bath at 480° C., a gas feed consisting of 3 propane/0.69 ammonia/2.2 oxygen/2.2 nitrogen/1 water was introduced into the bottom of the reactor containing a promoted vanadium, antimony oxide propane ammoxidation catalyst diluted 50 wt % with quartz chips. The reactor was operated at atmospheric pressure and the weight hourly space velocity of the propane feed was 0.50 $hr^{-1}$. Propylene was introduced into the reactor at 49.1% of the level of the catalyst bed height. The overall ratio of propylene to propane fed to the reactor was 0.140/1. Conversion of propane plus propylene was 23.1%. Selectivities to useful products from propane and propylene were; 43.4% to acrylonitrile, 15.7% to acrolein, and 7.8% to acrylic acid (total useful product selectivity of 66.9%). The amount of ammonia breakthrough was reduced to 5.6% of the ammonia fed.

Comparative Example B

Using a 0.5 inch diameter titanium U-tube reactor positioned in a temperature controlled sand bath at 480° C., a gas feed consisting of 3 propane/0.69 ammonia/2.2 oxygen/2.2 nitrogen/1 water was introduced into the bottom of the reactor containing a promoted vanadium, antimony oxide propane ammoxidation catalyst diluted 50 wt % with quartz chips. The reactor was operated at atmospheric pressure and the weight hourly space velocity of the propane feed was 0.37 $hr^{-1}$. Propane conversion was 19.7%. Selectivity to acrylonitrile was 54.3%. Total useful product selectivity (i.e. acrylonitrile, acrolein, and acrylic acid) was about 56.1%. The amount of ammonia breakthrough was 16.8% of the ammonia fed.

A comparison of this Comparative Example B with Examples 7 through 10 shows that operating at feeds and conditions that provide for a low ammonia breakthrough (i.e. Comparative Example B) also yields lower overall selectivity to acrylonitrile. In contrast, by adding propylene to the reactor and operating in accordance with the instant invention (i.e. Examples 7 through 10), the overall selectivity to acrylonitrile is enhanced and the amount of ammonia breakthrough is further reduced.

EXAMPLE 7

Using a 0.5 inch diameter titanium U-tube reactor positioned in a temperature controlled sand bath at 480° C., a gas feed consisting of 3 propane/0.68 ammonia/2.2 oxygen/2.2 nitrogen/1 water was introduced into the bottom of the reactor containing a promoted vanadium, antimony oxide propane ammoxidation catalyst diluted 50 wt % with quartz chips. The reactor was operated at atmospheric pressure and the weight hourly space velocity of the propane feed was 0.38 $hr^{-1}$. Propylene was introduced into the reactor at 23.6% of the level of the catalyst bed height. The overall ratio of propylene to propane fed to the reactor was 0.032/1. Conversion of propane plus propylene was 19.8%. Selectivities to useful products from propane and propylene were: 55.7% to acrylonitrile, 0.2% to acrolein, and 1.7% to acrylic acid (total useful product selectivity of 57.6%). The amount of ammonia breakthrough was reduced to 14.3% of the ammonia fed.

EXAMPLE 8

Using a 0.5 inch diameter titanium U-tube reactor positioned in a temperature controlled sand bath at 480° C., a gas feed consisting of 3 propane/0.67 ammonia/2.2 oxygen/2.2 nitrogen/1 water was introduced into the bottom of the reactor containing a promoted vanadium, antimony oxide propane ammoxidation catalyst diluted 50 wt % with quartz chips. The reactor was operated at atmospheric pressure and the weight hourly space velocity of the propane feed was 0.52 $hr^{-1}$. Propylene was introduced into the reactor at 23.6% of the level of the catalyst bed height. The overall ratio of propylene to propane fed to the reactor was 0.105/1. Conversion of propane plus propylene was 20.0%. Selectivities to useful products from propane and propylene were: 53.5% to acrylonitrile, 0.6% to acrolein, and 3.7% to acrylic acid (total useful product selectivity of 57.8%). The amount of ammonia breakthrough was reduced to 10.0% of the ammonia fed.

EXAMPLE 9

Using a 0.5 inch diameter titanium U-tube reactor positioned in a temperature controlled sand bath at 480° C., a gas feed consisting of 3 propane/0.68 ammonia/2.2 oxygen/2.1 nitrogen/1 water was introduced into the bottom of the reactor containing two beds of a promoted vanadium, antimony oxide propane ammoxidation catalyst diluted 50 wt % with quartz chips. The upper bed contained 70% of the overall catalyst charge and the lower bed contained 30% of the overall catalyst charge. Propylene was introduced between the two beds into a layer of quartz chips that served as a mixing chamber for the propylene and the gas mixture in the reactor. The reactor was operated at atmospheric pressure and the weight hourly space velocity of the propane feed was 0.35 $hr^{-1}$. The overall ratio of propylene to propane fed to the reactor was 0.034/1. Conversion of propane plus propylene was 18.6%. Selectivities to useful products from propane and propylene were: 60.3% to acrylonitrile, 0% to acrolein, and 0.2% to acrylic acid (total useful product selectivity of 60.5%). The amount of ammonia breakthrough was reduced to 14.8% of the ammonia fed.

EXAMPLE 10

Using a 0.5 inch diameter titanium U-tube reactor positioned in a temperature controlled sand bath at 480° C., a gas feed consisting of 3 propane/0.67 ammonia/2.2 oxygen/2.2 nitrogen/1 water was introduced into the bottom of the reactor containing two beds of a promoted vanadium, antimony oxide propane ammoxidation catalyst diluted 50 wt % with quartz chips. The upper bed contained 70% of the overall catalyst charge and the lower bed contained 30% of the overall catalyst charge. Propylene was introduced between the two beds into a layer of quartz chips that served as a mixing chamber for the propylene and the gas mixture in the reactor. The reactor was operated at atmospheric pressure and the weight hourly space velocity of the propane feed was 0.35 $hr^{-1}$. The overall ratio of propylene to propane fed to the reactor was 0.071/1. Conversion of propane plus propylene was 20.3%. Selectivities to useful products from propane and propylene were: 56.3% to acrylonitrile, 0.1% to acrolein, and 0.4% to acrylic acid (total useful product selectivity of 56.8%). The amount of ammonia breakthrough was reduced to 9.6% of the ammonia fed.

Comparative Example C

Using a 0.5 inch diameter titanium U-tube reactor positioned in a temperature controlled sand bath at 480° C., a gas feed consisting of 3 propane/0.81 ammonia/2.2 oxygen/2.2 nitrogen/1 water was introduced into the bottom of the reactor containing a promoted vanadium, antimony oxide propane ammoxidation catalyst. The reactor was operated at atmospheric pressure and the weight hourly space velocity of the propane feed was 0.45 hr$^{-1}$. Propane conversion was 20.4%. Selectivity to acrylonitrile was 55.1%. Total useful product selectivity (i.e. acrylonitrile, acrolein, and acrylic acid) was about 55.9%. The amount of ammonia breakthrough was 21.7% of the ammonia fed.

EXAMPLE 11

Using a 0.5 inch diameter titanium U-tube reactor positioned in a temperature controlled sand bath at 480° C., a gas feed consisting of 3 propane/0.84 ammonia/2.2 oxygen/2.2 nitrogen/1 water was introduced into the bottom of the reactor containing two beds of a promoted vanadium, antimony oxide propane ammoxidation catalyst. The upper bed contained 20% of the overall catalyst charge and the lower bed contained 80% of the overall catalyst charge. Propylene was introduced between the two beds into a layer of quartz chips that served as a mixing chamber for the propylene and the gas mixture in the reactor. The reactor was operated at atmospheric pressure and the weight hourly space velocity of the propane feed was 0.36 hr$^{-1}$. The overall ratio of propylene to propane fed to the reactor was 0.032/1. Conversion of propane plus propylene was 22.4%. Selectivities to useful products from propane and propylene were: 54.5% to acrylonitrile, 0.6% to acrolein, and 1.6% to acrylic acid (total useful product selectivity of 56.7%). The amount of ammonia breakthrough was reduced to 16.9% of the ammonia fed.

Comparative Example D

Using a 0.5 inch diameter titanium U-tube reactor positioned in a temperature controlled sand bath at 480° C., a gas feed consisting of 3 propane/0.82 ammonia/2.2 oxygen/2.2 nitrogen/1 water was introduced into the bottom of the reactor containing a promoted vanadium, antimony oxide propane ammoxidation catalyst. The reactor was operated at atmospheric pressure and the weight hourly space velocity of the propane feed was 0.41 hr$^{-1}$. Propane conversion was 19.9%. Selectivity to acrylonitrile was 58.1%. Total useful product selectivity (i.e. acrylonitrile, acrolein, and acrylic acid) was about 58.6%. The amount of ammonia breakthrough was 23.5% of the ammonia fed.

Comparative Example E

Using a 0.5 inch diameter titanium U-tube reactor positioned in a temperature controlled sand bath at 480° C., a gas feed consisting of 3 propane/0.83 ammonia/2.2 oxygen/2.2 nitrogen/1 water was introduced into the bottom of the reactor containing a promoted vanadium, antimony oxide propane ammoxidation catalyst. The reactor was operated at atmospheric pressure and the weight hourly space velocity of the propane feed was 0.41 hr$^{-1}$. Propane conversion was 20.1%. Selectivity to acrylonitrile was 58.0%. Total useful product selectivity (i.e. acrylonitrile, acrolein, and acrylic acid) was about 58.6%. The amount of ammonia breakthrough was 22.5% of the ammonia fed.

EXAMPLE 12

Using a 0.5 inch diameter titanium U-tube reactor positioned in a temperature controlled sand bath at 480° C., a gas feed consisting of 3 propane/0.79 ammonia/2.2 oxygen/2.2 nitrogen/1 water was introduced into the bottom of the reactor containing two beds of a promoted vanadium, antimony oxide propane ammoxidation catalyst. The upper bed contained 40% of the overall catalyst charge and the lower bed contained 60% of the overall catalyst charge. Propylene was introduced between the two beds into a layer of quartz chips that served as a mixing chamber for the propylene and the gas mixture in the reactor. The reactor was operated at atmospheric pressure and the weight hourly space velocity of the propane feed was 0.36 hr$^{-1}$. The overall ratio of propylene to propane fed to the reactor was 0.047/1. Conversion of propane plus propylene was 22.2%. Selectivities to useful products from propane and propylene were: 56.3% to acrylonitrile, 0.1% to acrolein, and 1.6% to acrylic acid (total useful product selectivity of 57.9%). The amount of ammonia breakthrough was reduced to 14.0% of the ammonia fed.

EXAMPLE 13

Using a 0.5 inch diameter titanium U-tube reactor positioned in a temperature controlled sand bath at 480° C., a gas feed consisting of 3 propane/0.79 ammonia/2.2 oxygen/2.2 nitrogen/1 water was introduced into the bottom of the reactor containing two beds of a promoted vanadium, antimony oxide propane ammoxidation catalyst. The upper bed contained 40% of the overall catalyst charge and the lower bed contained 60% of the overall catalyst charge. Propylene was introduced between the two beds into a layer of quartz chips that served as a mixing chamber for the propylene and the gas mixture in the reactor. The reactor was operated at atmospheric pressure and the weight hourly space velocity of the propane feed was 0.36 hr$^{-1}$. The overall ratio of propylene to propane fed to the reactor was 0.052/1. Conversion of propane plus propylene was 22.3%. Selectivities to useful products from propane and propylene were: 56.2% to acrylonitrile, 0.2% to acrolein, and 1.9% to acrylic acid (total useful product selectivity of 58.3%). The amount of ammonia breakthrough was reduced to 13.2% of the ammonia fed.

EXAMPLE 14

Using a 0.5 inch diameter titanium U-tube reactor positioned in a temperature controlled sand bath at 480° C., a gas feed consisting of 3 propane/0.78 ammonia/2.2 oxygen/2.2 nitrogen/1 water was introduced into the bottom of the reactor containing two beds of a promoted vanadium, antimony oxide propane ammoxidation catalyst. The upper bed contained 40% of the overall catalyst charge and the lower bed contained 60% of the overall catalyst charge. Propylene was introduced between the two beds into a layer of quartz chips that served as a mixing chamber for the propylene and the gas mixture in the reactor. The reactor was operated at atmospheric pressure and the weight hourly space velocity of the propane feed was 0.44 hr$^{-1}$. The overall ratio of propylene to propane fed to the reactor was 0.052/1. Conversion of propane plus propylene was 19.4%. Selectivities to useful products from propane and propylene were: 57.0% to acrylonitrile, 0.4% to acrolein, and 1.3% to acrylic acid (total useful product selectivity of 58.7%). The amount of ammonia breakthrough was reduced to 15.5% of the ammonia fed.

The claimed invention is:

1. A method for the reduction of ammonia breakthrough during the manufacture of acrylonitrile comprising introducing a hydrocarbon selected from the group consisting of propane and isobutane; ammonia and an oxygen-containing gas into a lower portion of a fluid-bed reactor containing an ammoxidation catalyst to react in the presence of said catalyst to produce acrylonitrile wherein the improvement comprises introducing into the reactor at least one $C_2$ to $C_5$ olefin which will react with at least a portion of the unreacted ammonia and oxygen present in the reactor to substantially reduce the amount of ammonia present in the reactor effluent exiting the reactor.

2. The process of claim 1, wherein the hydrocarbon is selected to be propane.

3. The process of claim 1, wherein the $C_2$–$C_5$ olefin is propylene.

4. The process of claim 1, wherein the reactor is a fluid-bed reactor.

5. The process of claim 4, wherein the olefin is introduced into the fluid-bed reactor at a location above at least 20% of the expanded fluid catalytic bed height.

6. The process of claim 4, wherein the olefin is introduced into the fluid-bed reactor at a location above at least 50% of the expanded fluid catalytic bed height.

7. The process of claim 4, wherein the olefin is introduced into the fluid-bed reactor at a location above at least 80% of the expanded fluid catalytic bed height.

8. The process of claim 1, wherein the catalyst is of the formula:

$$V_v Sb_m A_a D_d O_x$$

wherein A, when present, is at least one of Sn, Ti, and Fe,

D, when present, is at least one of Li, Mg, Na, Ca, Sr, Ba, Co, Cr, Ga, Ni, Zn, Ge, Nb, Zr, Mo, W, Cu, Te, Ta, Se, Bi, Ce, In, As, B, Al, and Mn.

V is 1 m is 0.5 to 10 a is 0 to 10 d is 0 to 10 x is a value sufficient to satisfy the valence requirements of the other elements present.

9. A method for the conversion of propylene based feedstock acrylonitrile manufacturing process, wherein propylene, ammonia and oxygen are reacted in a reactor in the presence of a catalyst to produce acrylonitrile, to a propane based feedstock acrylonitrile manufacturing process, wherein propane, ammonia and oxygen are reacted in the presence of a catalyst to produce acrylonitrile, the method comprising (a) substituting a propane based feedstock for the propylene based feedstock, (b) introducing into the reactor at least one $C_2$ to $C_5$ olefin which will react with at least a portion of unreacted ammonia and oxygen present in the reactor to substantially reduce the amount of ammonia present in the reactor effluent exiting the reactor, and (c) adding to the process a means for the separation, recovery and recycle of unreacted propane.

10. The method of claim 9, wherein the catalyst in the reactor is replaced with a catalyst of the formula $$V_v Sb_m A_a D_d O_x$$

wherein A, when present, is at least one of Sn, Ti, and Fe,

D, when present, is at least one of Li, Mg, Na, Ca, Sr, Ba, Co, Cr, Ga, Ni, Zn, Ge, Nb, Zr, Mo, W, Cu, Te, Ta, Se, Bi, Ce, In, As, B, Al, and Mn.

V is 1 m is 0.5 to 10 a is 0 to 10 d is 0 to 10 x is a value sufficient to satisfy the valence requirements of the other elements present.

11. The process of claim 9, wherein the $C_2$–$C_5$ olefin is propylene.

12. The process of claim 9, wherein the reactor is a fluid-bed reactor.

13. The process of claim 12, wherein the olefin is introduced into the fluid-bed reactor at a location above at least 20% of the expanded fluid catalytic bed height.

14. The process of claim 12, wherein the olefin is introduced into the fluid-bed reactor at a location above at least 50% of the expanded fluid catalytic bed height.

15. The process of claim 12, wherein the olefin is introduced into the fluid-bed reactor at a location above at least 80% of the expanded fluid catalytic bed height.

* * * * *

UNITED STATES PATENT AND TRADEMARK OFFICE
CERTIFICATE OF CORRECTION

PATENT NO. : 6,262,290 B1
DATED : July 17, 2001
INVENTOR(S) : James F. Brazdil, Jr., Joseph P. Padolewski It is certified that error appears in the above-identified patent and that said Letters Patent is hereby corrected as shown below:

<u>Column 2,</u>
Line 59, "the $C_2$-$C_5$, olefin allows" should read -- the $C_2$-$C_5$ olefin allows --

<u>Column 3,</u>
Line 35, "a point ownstream from the" should read -- a point downstream from the --
Line 36, "to react ith substantially all" should read -- to react with substantially all --

Signed and Sealed this

Twenty-sixth Day of February, 2002

Attest:

JAMES E. ROGAN
Attesting Officer *Director of the United States Patent and Trademark Office*